US00PP28940P2

(12) United States Plant Patent
Schroll

(10) Patent No.: US PP28,940 P2
(45) Date of Patent: Feb. 6, 2018

(54) ***HYDRANGEA* PLANT NAMED 'SCHROLL88-09-02'**

(50) Latin Name: *Hydrangea macrophylla*
Varietal Denomination: SCHROLL88-09-02

(71) Applicant: Soren Schroll, Odense SV (DK)

(72) Inventor: Soren Schroll, Odense SV (DK)

(73) Assignee: Scholl Management ApS, Odense SV (DK)

( * ) Notice: Subject to any disclaimer, the term of this patent is extended or adjusted under 35 U.S.C. 154(b) by 0 days.

(21) Appl. No.: 15/330,429

(22) Filed: Sep. 20, 2016

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — C. A. Whealy

(57) ABSTRACT

A new and distinct cultivar of *Hydrangea* plant named 'SCHROLL88-09-02', characterized by its compact, upright and mounded plant habit; moderately vigorous growth habit; freely branching habit and strong stems; relatively small leaves; large mophead-type inflorescences; dark purple-colored sterile flowers that are initially light yellow green in color when plants are treated with aluminum sulfate; and early and long flowering period.

2 Drawing Sheets

Botanical designation: *Hydrangea macrophylla.*
Cultivar denomination: 'SCHROLL88-09-02'.

BACKGROUND OF THE INVENTION

The present invention relates to a new and distinct cultivar of *Hydrangea* plant, botanically known as *Hydrangea macrophylla* and hereinafter referred to by the name 'SCHROLL88-09-02'.

The new *Hydrangea* plant is a product of a planned breeding program conducted by the Inventor in Aarslev, Denmark. The objective of the breeding program was to develop new container-type *Hydrangea* plants with strong stems, early flowering response and attractive leaf and flower coloration.

The new *Hydrangea* plant is a naturally-occurring whole plant mutation of *Hydrangea macrophylla* 'SchrollA02', not patented. The new *Hydrangea* plant was discovered and selected by the Inventor in 2014 as a single flowering plant from within a population of plants of 'SchrollA02' in a controlled greenhouse environment in Aarslev, Denmark.

Asexual reproduction of the new cultivar by softwood cuttings in Aarslev, Denmark since 2014 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SCHROLL88-09-02'. These characteristics in combination distinguish 'SCHROLL88-09-02' as a new and distinct *Hydrangea* plant:

1. Compact, upright and mounded plant habit.
2. Moderately vigorous growth habit.
3. Freely branching habit and strong stems.
4. Relatively small leaves.
5. Large mophead-type inflorescences.
6. Dark purple-colored sterile flowers that are initially light yellow green in color when plants are treated with aluminum sulfate.
7. Early and long flowering period.

Plants of the new *Hydrangea* differ primarily from plants of the mutation parent, 'SchrollA02', in the following characteristics:

1. Plants of the new *Hydrangea* are more compact than and not as vigorous as plants of 'SchrollA02'.
2. Inflorescences of plants of the new *Hydrangea* are more rounded than and not as flat as inflorescences of plants of 'SchrollA02'.
3. Plants of the new *Hydrangea* and 'SchrollA02' differ in sterile flower color as plants of 'SchrollA02' have sterile flowers that are blue in color when treated with aluminum sulfate.

Plants of the new *Hydrangea* can be compared to plants of *Hydrangea macrophylla* 'H213901', disclosed in U.S. Plant Pat. No. 26,221. Plants of the new *Hydrangea* differ primarily from plants of 'H213901' in the following characteristics:

1. Plants of the *Hydrangea* are less vigorous than plants of 'H213901'.
2. Plants of the new *Hydrangea* flower earlier than plants of 'H213901'.
3. Inflorescences of plants of the new *Hydrangea* have more sterile flowers than inflorescences of plants of 'H213901'.

4. Sterile flowers of plants of the new *Hydrangea* are flatter than and not as folded and curly as sterile flowers of plants of 'H213901'.
5. Plants of the new *Hydrangea* and 'H213901' differ in sterile flower color as plants of 'H213901' have sterile flowers that are medium blue and medium purple in color when treated with aluminum sulfate.

Plants of the new *Hydrangea* can be compared to plants of *Hydrangea macrophylla* 'H213906', disclosed in U.S. Plant Pat. No. 26,509. Plants of the new *Hydrangea* differ primarily from plants of 'H213906' in the following characteristics:

1. Plants of the *Hydrangea* are less vigorous than plants of 'H213906'.
2. Plants of the new *Hydrangea* flower later than plants of 'H213906'.
3. Plants of the new *Hydrangea* and 'H213906' differ in sterile flower color as plants of 'H213906' have sterile flowers that are clear blue in color when treated with aluminum sulfate.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'SCHROLL88-09-02' grown in a container.

The photograph on the second sheet is a close-up view of a typical developing inflorescence of 'SCHROLL88-09-02' (top of sheet) and a developed inflorescence of 'SCHROLL88-09-02' (bottom of sheet).

DETAILED BOTANICAL DESCRIPTION

Plants used in the aforementioned photographs and in the following description were grown during the spring in 13-cm containers in a glass-covered greenhouse in Aarslev, Denmark and under cultural practices typical of commercial *Hydrangea* production. Plants of the new *Hydrangea* were pinched one time and were one year old when the photographs and description were taken. During the production of the plants, day temperatures ranged from 15° C. to 25° C., night temperatures ranged from 10° C. to 20° C. and light levels ranged from 40 to 50 klux. Plants used for the description and photographs were treated with aluminum sulfate to "blue" the inflorescences. In the following description, color references are made to The Royal Horticultural Society Colour Chart, 2007 Edition, except where general terms of ordinary dictionary significance are used.

Botanical description: *Hydrangea macrophylla* 'SCHROLL88-09-02'.

Parentage: Naturally-occurring whole plant mutation of *Hydrangea macrophylla* 'SchrollA02', not patented.

Propagation:

*Type cutting*.—By softwood cuttings.

*Time to initiate roots, summer*.—About ten days at temperatures about 18° C. to 22° C.

*Time to initiate roots, winter*.—About two weeks at temperatures about 18° C. to 20° C.

*Time to produce a rooted young plant, summer*.—About four weeks at temperatures about 18° C. to 20° C.

*Time to produce a rooted young plant, winter*.—About five weeks at temperatures about 18° C. to 20° C.

*Root description*.—Medium in thickness, fibrous; white, close to N155D, in color.

*Rooting habit*.—Low branching; sparse.

Plant description:

*Plant and growth habit*.—Perennial subshrub; compact, upright and mounded plant habit; broadly inverted triangle; freely branching habit with about four to six lateral branches developing per plant; strong lateral branches; moderately vigorous growth habit.

*Plant height*.—About 35 cm to 45 cm.

*Plant diameter or area of spread*.—About 30 cm to 40 cm.

*Lateral branches*.—Length: About 25 cm to 30 cm. Diameter: About 3 mm to 6 mm. Internode length: About 7 cm. Strength: Strong. Texture: Smooth, glabrous; becoming woody with development. Color, developing: Close to 144A. Color, developed: Close to 199B. Color, lenticels: Close to N199B.

Leaf description:

*Arrangement*.—Opposite, simple.

*Length*.—About 8 cm to 11 cm.

*Width*.—About 6 cm to 8 cm.

*Shape*.—Ovate.

*Apex*.—Acute or sub-acuminate.

*Base*.—Obtuse to rounded.

*Margin*.—Serrate.

*Texture and luster, upper surface*.—Rugose, glabrous; moderately glossy.

*Texture and luster, lower surface*.—Rough, glabrous; prominent venation; matte.

*Venation pattern*.—Pinnate, reticulate.

*Color*.—Developing leaves, upper surface: Close to 137A. Developing leaves, lower surface: Close to 137D. Fully expanded leaves, upper surface: Close to 137B; venation, close to 146B. Fully expanded leaves, lower surface: Close 146B; venation, close to 146C.

*Petioles*.—Length: About 2 cm to 4 cm. Diameter: About 2 mm to 4 mm. Strength: Strong. Texture, upper and lower surfaces: Smooth, glabrous. Color, upper surface: Close to 146B. Color, lower surface: Close to 146A.

Inflorescence & flower description:

*Flower type and habit*.—Showy single sterile and inconspicuous single fertile flowers arranged on terminal mophead-type panicles; panicles hemispherical to flattened globular in overall shape; fertile flowers face mostly upright and sterile flowers face upright to outwardly; early flowering habit, plants begin flowering about ten and twelve weeks after planting during the summer and winter, respectively.

*Natural flowering season*.—Continuous flowering during the summer in Northern Europe.

*Flower longevity, fertile flowers*.—Flowers last less than one month; fertile flowers not persistent.

*Flower longevity, sterile flowers*.—Long flowering period, flowers last about four months on the plant; sterile flowers persistent.

*Quantity of flowers*.—Freely flowering habit with about 30 to 40 fertile flowers and about 100 sterile flowers per panicle.

*Fragrance*.—None detected.

*Panicle height*.—About 6 cm to 8 cm.

*Panicle diameter*.—About 14 cm to 17 cm.

*Flower diameter, fertile flowers*.—About 8 mm.

*Flower depth (height), fertile flowers*.—About 4 mm.

*Flower diameter, sterile flowers*.—About 5 cm to 6 cm.

*Flower depth (height), sterile flowers*.—About 1 cm.

*Flower shape, fertile flowers*.—Deltoid.

*Flower shape, sterile flowers*.—Deltoid.

*Flower buds, fertile flowers*.—Length: About 3 mm. Diameter: About 2 mm to 3 mm. Shape: Flattened globular. Color: Close to 144B.

*Flower buds, sterile flowers*.—Length: About 3.5 mm. Diameter: About 3 mm to 5 mm. Shape: Flattened globular. Color: Close to 144C becoming closer to 92A with development.

*Petals, fertile flowers only*.—Quantity and arrangement: Four or five in a single whorl; valvate. Length: About 3.5 mm. Width: About 2 mm. Shape: Elliptical. Apex: Subacute. Base: Rounded. Margin: Entire. Texture, upper and lower surfaces: Smooth, glabrous. Color: When opening, upper and lower surfaces: Close to 149B. Fully opened, upper and lower surfaces: Close to 98A; color does not change with development.

*Sepals, fertile flowers*.—Quantity and arrangement: Four to five in a single whorl; valvate. Length: About 2.5 mm. Width: About 2 mm. Shape: Elliptical. Apex: Subacute. Base: Rounded. Margin: Entire. Texture, upper and lower surfaces: Smooth, glabrous. Color: When opening, upper and lower surfaces: Close to 98A. Fully opened, upper and lower surfaces: Close to 98A; color does not change with development.

*Sepals, sterile flowers*.—Quantity and arrangement: Four to five in a single whorl; imbricate. Length: About 1.8 cm to 2.2 cm. Width: About 1.8 cm to 2.2 cm. Shape: Deltoid. Apex: Subacute. Base: Cordate to rounded. Margin: Entire. Texture, upper surface: Smooth, glabrous. Texture, lower surface: Rugose, glabrous. Color: When opening, upper and lower surfaces: Close to 149D. Fully opened, upper surface: Close to 83A and 79A to 79B; color does not change with development. Fully opened, lower surface: Close to 79C; color does not change with development.

*Pedicels, fertile flowers*.—Length: About 3 mm to 4 mm. Diameter: About 1 mm. Strength: Moderately strong. Aspect: About 35° to 40° from vertical. Texture: Smooth, glabrous. Color: Close to N79C.

*Pedicels, sterile flowers*.—Length: About 2 cm to 3 cm. Diameter: About 1.5 mm to 2 mm. Strength: Strong. Aspect: About 35° to 40° from vertical. Texture: Smooth, glabrous. Color: Close to N79C.

*Reproductive organs, fertile flowers only*.—Stamens: Quantity per flower: About eight or rarely, ten. Filament length: About 1 mm to 2 mm. Filament color: Close to 98A. Anther length: About 1 mm to 2 mm. Anther shape: Two-lobed, conical. Anther color: Close to 98A. Pollen amount: Abundant. Pollen color: Close to 155D. Pistils: Pistil quantity per flower: About three. Pistil length: About 2 mm to 2.5 mm. Stigma shape: Club-shaped, thick. Stigma color: Close to 160C. Style length: About 1 mm. Style color: Close to 160C.

*Seeds*.—Quantity: Numerous. Color: Close to 200C.

Disease & pest resistance: Plants of the new *Hydrangea* have been observed to be resistant to spider mites and aphids; plants of the new *Hydrangea* have not been observed to be resistant to pathogens and other pests common to *Hydrangea* plants.

Temperature tolerance: Plants of the new *Hydrangea* have been shown to be tolerant to temperatures ranging from −5° C. to 35° C.

It is claimed:

1. A new and distinct *Hydrangea* plant named 'SCHROLL88-09-02' as illustrated and described.

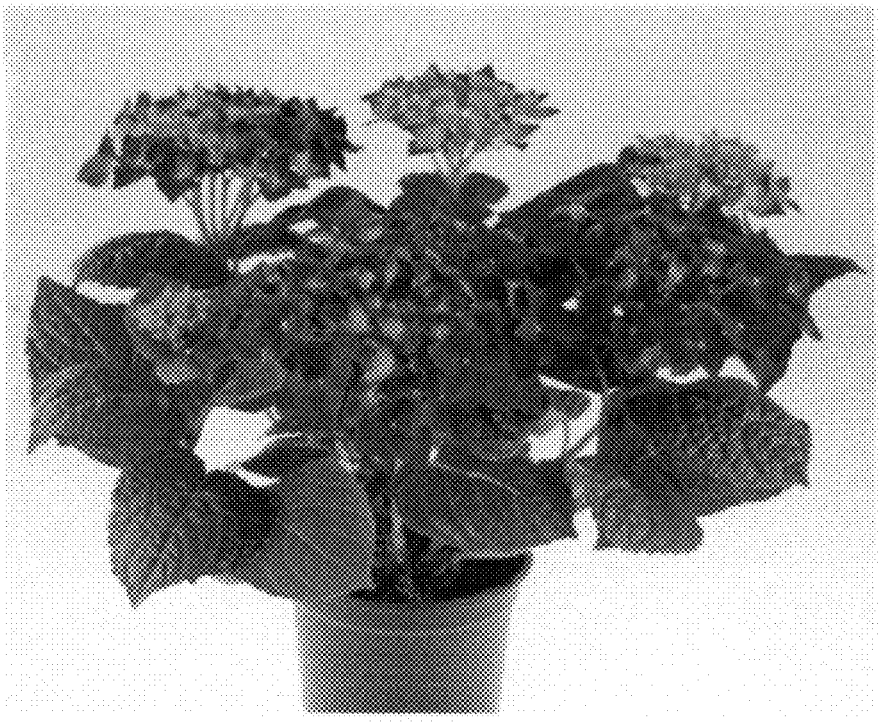

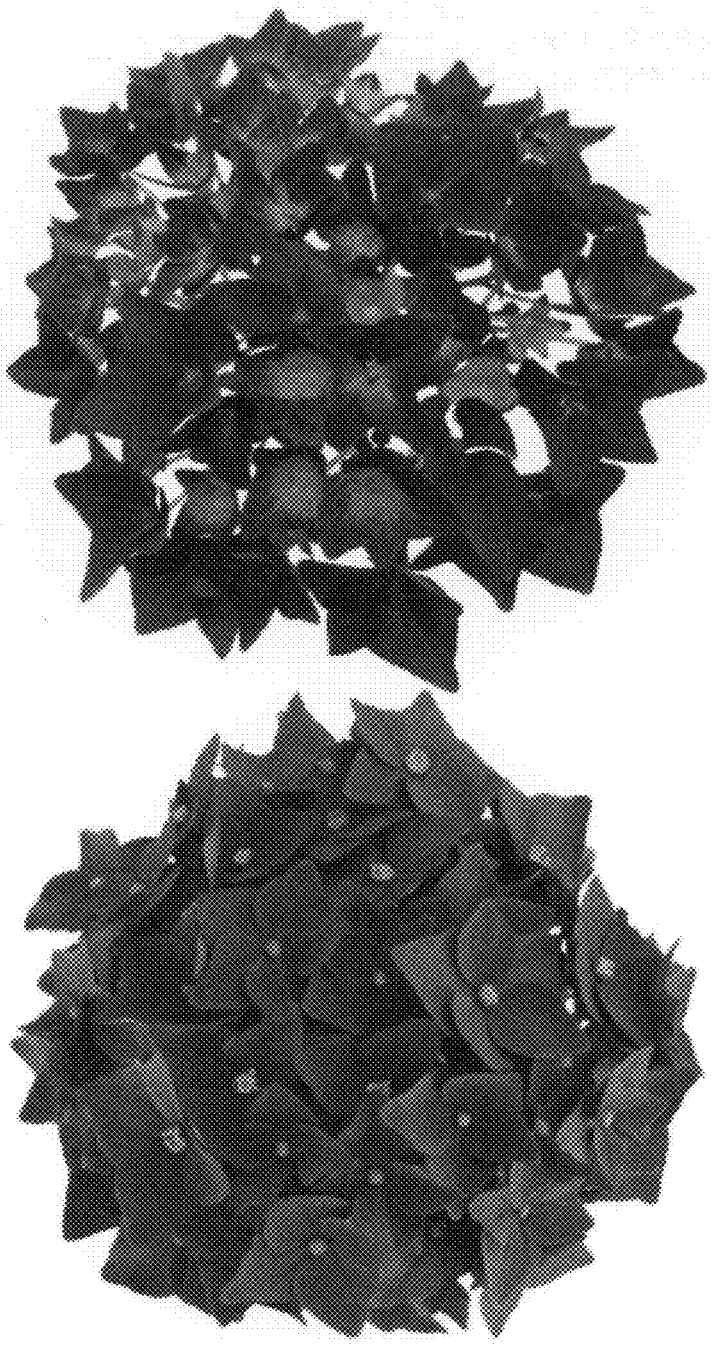

* * * * *